United States Patent
Matsui et al.

[11] 3,983,134
[45] Sept. 28, 1976

[54] UREYLENETHIOPHANES AND THEIR RELATED COMPOUNDS, AND PRODUCTION THEREOF

[75] Inventors: Masanao Matsui, Tokyo; Kenji Mori, Kawasaki; Takeshi Kitahara, Tokyo; Seiichi Kitamura, Ibaraki; Kazumasa Ohba, Itami, all of Japan

[73] Assignee: Teikoku Chemical Industry Co., Ltd., Osaka, Japan

[22] Filed: Aug. 5, 1975

[21] Appl. No.: 602,178

[30] Foreign Application Priority Data
Aug. 5, 1974   Japan.................................. 49-90112
Aug. 6, 1974   Japan.................................. 49-90613
Aug. 8, 1974   Japan.................................. 49-91685

[52] U.S. Cl. .................. 260/309.7; 260/329 AM; 260/332.1; 260/332.2 R; 260/347.3; 260/347.4
[51] Int. Cl.² ........................................ C07D 49/34
[58] Field of Search ................................ 260/309.7

[56] References Cited
UNITED STATES PATENTS

| | | | |
|---|---|---|---|
| 2,489,237 | 11/1949 | Goldberg et al. | 260/309.7 X |
| 2,492,373 | 12/1949 | Wood et al. | 260/309.7 X |
| 2,506,594 | 5/1950 | Hoffman | 260/309.7 X |

*Primary Examiner*—Ethel G. Love
*Attorney, Agent, or Firm*—Jones, Tullar & Cooper

[57] ABSTRACT

Ureylenethiophanes and their related compounds of the formula:

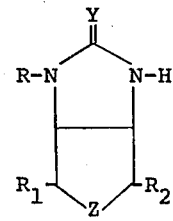

having a cis-configuration on the ureylene or thioureylene juncture, which are useful as the intermediates in the synthesis of biologically active biotin and its related compounds, can be produced selectively by reacting the corresponding compounds of the formula:

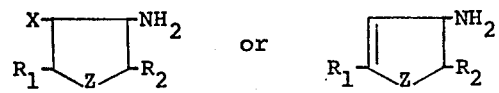

with isocyanates or isothiocyanates wherein R is a hydrogen atom, an alkyl group or an aralkyl group, $R_1$ and $R_2$ are each a hydrogen atom or an aliphatic hydrocarbon group bearing or not a carboxyl group or any other group convertible thereto at the terminal position, X is a halogen atom, Y is an oxygen atom or a sulfur atom and Z is an oxygen atom, a sulfur atom, a sulfinyl group or a sulfonyl group.

7 Claims, No Drawings

UREYLENETHIOPHANES AND THEIR RELATED COMPOUNDS, AND PRODUCTION THEREOF

The present invention relates to ureylenethiophanes and their related compounds, and production thereof. More particularly, it relates to ureylenethiophanes and their related compounds having a cis-configuration on the ureylene juncture which are useful as intermediates in the synthesis of biologically active biotin and its related compounds, and their production.

Biotin (also called "Vitamin H") is a valuable substance exerting a growth promoting effect as well as a preventive and therapeutic effect on dermatoses, etc.

For production of biotin, there have been proposed a number of methods. However, those are industrially unsatisfactory in requiring lengthy and troublesome steps, using expensive reagents, yielding objective biotin only in poor yields, etc.

Recently, Ellis et al. reported the successful production of 3,4-ureylenethiophane-1,1-dioxide, which is a key intermediate in the synthesis of biotin, from sulfolene in a few steps [J. Chem. Soc. Perkin I., 1972, 1560]. While this process is quite favorable in affording such valuable intermediate from the simple starting material, i.e. sulfolene, in a good yield via short steps, it is defective in that the obtained 3,4-ureylenethiophane-1,1-dioxide takes a trans-configuration on the ureylene juncture.

As the result of the extensive study, there has now been successfully accomplished the selective production of ureylenethiophanes and their related compounds having a cis-configuration on the ureylene juncture.

Accordingly, a basic object of the present invention is to provide ureylenethiophanes and their related compounds having a cis-configuration on the ureylene juncture. Another object of this invention is to provide ureylenethiophanes and their related compounds useful as intermediates in the synthesis of biologically active biotin and its related compounds. A further object of the invention is to provide a process for selective production of ureylenethiophanes and their related compounds having a cis-configuration on the ureylene juncture. These and other objects of the invention will be apparent to those skilled in the art from the foregoing and subsequent descriptions.

The objective compounds of the invention are ureylenethiophanes and their related compounds of the formula:

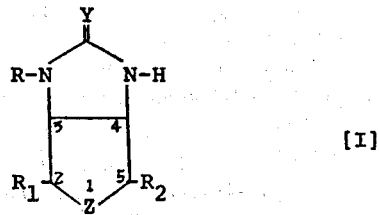

[I]

wherein R is a hydrogen atom, a lower alkyl group (e.g. methyl, ethyl, propyl, isopropyl, butyl) or an ar(lower)alkyl group such as phenyl(lower)alkyl (e.g. benzyl, phenylethyl) or naphthyl(lower)alkyl (e.g. naphthylmethyl, naphthylethyl), $R_1$ and $R_2$ are each a hydrogen atom or an aliphatic hydrocarbon group having not more than 10 carbon atoms and bearing or not a carboxyl group or any other group convertible thereto at the terminal position, Y is an oxygen atom or a sulfur atom and Z is an oxygen atom, a sulfur atom, a sulfinyl group or a sulfonyl group.

The term "lower" hereinabove and hereinafter used is intended to mean the one having not more than 5 carbon atoms. Examples of the aliphatic hydrocarbon group bearing or not a carboxyl group are alkyl (e.g. methyl, ethyl, propyl, isopropyl, butyl), carboxyalkyl (e.g. carboxymethyl, carboxyethyl, carboxypropyl, carboxybutyl), etc. As the group convertible to carboxyl, there may be exemplified esterified carboxyl such as lower alkoxycarbonyl or ar(lower)alkoxycarbonyl, cyano, carbamoyl, formyl, etc.

According to the present invention, the said objective compound [I] can be produced by reacting the corresponding compound of the formula:

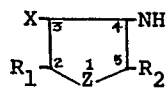 or 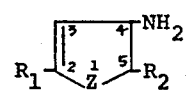

[IIA]          [IIB]

wherein X is a halogen atom (e.g. chlorine, bromine), and $R_1$, $R_2$ and Z are each as defined above with an isocyanate or isothiocyanate of the formula:

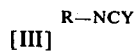

[III]

wherein R and Y are each as defined above.

As the isocyanate or isothiocyanate [III], there may be exemplified isocyanic acid, isothiocyanic acid, lower alkyl isocyanate, lower alkyl isothiocyanate, ar(lower)alkyl isocyanate, ar(lower)alkyl isothiocyanate, etc. In case of using isocyanic acid or isothiocyanic acid, it is usually employed in the form of ammonium salt, alkali metal salt (e.g. sodium salt, potassium salt) or alkaline earth metal salt (e.g. barium salt, magnesium salt).

The reaction may be carried out in the presence or absence of any solvent. Examples of the solvent are water, tetrahydrofuran, dioxane, methanol, ethanol, etc. For the reaction, a wide range of temperature from room temperature to the refluxing temperature of the reaction system may be adopted, and a higher temperature is usually preferred in completion of the reaction within a shorter period of time.

In the reaction, the isocyanate or isothiocyanate [III] is usually employed in an amount of from about 2 to 3 mols to 1 mol of the starting compound [IIA] or [IIB] so that the objective compound [I] can be produced directly. When the amount of the isocyanate or isothiocyanate [III] is smaller, for instance, in a nearly equimolar amount, there may be once produced as the main product the corresponding intermediary compound bearing at the 4-position a group of the formula: —NHCYNHR (wherein R and Y are each as defined above), which can be readily converted into the objective compound [I] by heating, for instance, in an appropriate medium (e.g. water, tetrahydrofuran, dioxane, methanol, ethanol) at a temperature under which the reaction system is refluxed.

Still, the starting compound [IIA] or [IIB] may be subjected to the said reaction as such or in the form of acid addition salt such as hydrohalide. Since the starting compound [IIA] or [IIB] may be sometimes resinified and such resinification can be prevented when kept in the form of acid addition salt, the use of the compound [IIA] or [IIB] in the acid addition salt form is ordinarily preferred.

The starting compounds [IIA] and [IIB] can be produced, for instance, according to the following scheme:

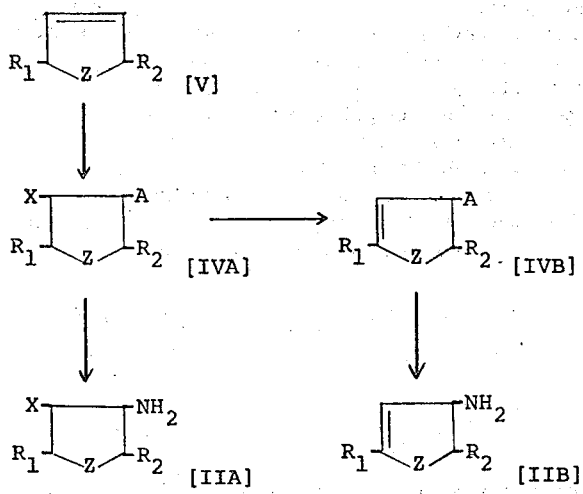

wherein A is a group convertible into amino, and $R_1$, $R_2$, X and Z are each as defined above.

Examples of the compound [V] are sulfolene, 2,5-dihydrothiophene, 2,5-dihydrofuran, etc.

The conversion of the compound [V] into the compound [IVA] may be carried out by reacting the former with lower alkyl halocarbamate (e.g. methyl N-chlorocarbamate, ethyl N-chlorocarbamate, methyl N,N-dichlorocarbamate, ethyl N,N-dichlorocarbamate) at a temperature from room temperature to the refluxing temperature of the reaction system. When desired, any inert solvent such as benzene, toluene, xylene, ether or tetrahydrofuran may be used as the reaction medium. Preferably, the reaction is performed in an inert gas atmosphere such as nitrogen, argon or neon.

In place of the lower alkyl halocarbamate, there may be used any other reagent which can introduce a halogen atom and a group A into the 3- and 4-positions, respectively. Examples of such reagent are lower alkyl haloamidosulfonate (e.g. methyl N-chloroamidosulfonate, ethyl N,N-dichloroamidosulfonate), ar(lower)alkyl haloamidosulfonate (e.g. benzyl N-chloroamidosulfonate, phenethyl N,N-dichloroamidosulfonate), halophthalimide (e.g. N-chlorophthalimide), halo(lower-)alkanedicarbimide (e.g. N-chlorosuccinimide), halocyanamide (e.g. N-chlorocyanamide, N,N-dichlorocyanamide), the combination of halogen and cyanamide, etc.

The compound [IVA] can be converted into the compound [IVB] by treatment of the former with a hydrogen halide-eliminating agent such as a base (e.g. sodium hydroxide, sodium carbonate, sodium bicarbonate, triethylamine) in an inert solvent (e.g. methanol, ethanol, propanol, isopropanol, butanol, ethylene gylcol) at an elevated temperature, for instance, from about 60° to 100°C.

For conversion of the compound [IVA] or [IVB] into the compound [IIA] or [IIB], the former may be subjected to any appropriate treatment for converting the group A into amino. When, for instance, the group A is —NHCOOR' (wherein R' is lower alkyl), the compound [IVA] or [IVB] may be treated with a mineral acid (e.g. hydrochloric acid, hydrobromic acid, hydroiodic acid, sulfuric acid) in an aqueous medium, usually while refluxing. Depending on the kind of the group A, any other procedure such as hydrolysis with an acid or a base, hydrogenolysis or reduction may be appropriately chosen.

As stated above, the compound [I] obtained by the process of this invention are structurally characteristic in having a cis-configuration on the ureylene or thioureylene juncture present at the 3- and 4-positions. Since naturally existing biotin has also such cis-configuration, the compounds [I] are particularly useful as intermediates in the synthesis of biologically active biotin or its related compounds such as biotin methyl ester, oxybiotin and biotin sulfoxide. For instance, the compound I: R = benzyl; $R_1 = R_2$ = hydrogen; Y = oxygen; Z = sulfur can be converted into biotin via the steps of benzylation, introduction of ω-carboxybutyl group and debenzylation. Further, for instance, the compound [I: R = $R_1$ = $R_2$ = hydrogen; Y = oxygen; Z = sulfonyl] can be converted into biotin via the steps of benzylation, introduction of ω-carboxybutyl group, reduction and debenzylation. An example of such conversion into biotin is described in Tetrahederon Letters, No. 10, 827 (1975).

Practical and presently preferred embodiments of the invention are illustratively shown in the following Examples.

EXAMPLE 1

A. Preparation of 3-chloro-4-ethoxycarbonylaminothiophane-1,1-dioxide

To a stirred suspension of sulfolene (150 g) in benzene (150 ml), N,N-dichlorourethane (200 g) was added dropwise at a rate sufficient to maintain the reaction temperature at 20° to 25°C under a nitrogen atmosphere. After the addition is completed, the reaction mixture was stirred at room temperature for 1 hour and then under reflux for 3.5 hours. To this reaction mixture, a 20% aqueous $NaHSO_3$ solution (400 ml) was added dropwise over a period of 1 hour with stirring at 5° to 10°C, and the resulting mixture was stirred for additional 1 hour. The precipitate was collected by filtration and washed with benzene and water. The benzene layer was washed with water and dried over anhydrous sodium sulfate. After removal of the solvent, the resulting oily residue was allowed to stand overnight, and precipitated crystals were collected by filtration. The combined yield of 3-chloro-4-ethoxycarbonylaminothiophane-1,1-dioxide was 114.5 g. M.P. 190°–191.5°C.

B. Preparation of 2,3-dehydro-4-ethoxycarbonylaminothiophane-1,1-dioxide

A mixture of 3-chloro-4-ethoxycarbonylaminothiophane-1,1-dioxide (10 g) and anhydrous sodium carbonate (5 g) in ethanol (30 ml) was stirred at 95° to 100°C for 2 hours. The reaction mixture was concentrated in vacuo to dryness. The residue was dissolved in water and extracted with ethyl acetate. The extract was washed with a saturated aqueous solution of sodium chloride and dried over anhydrous magnesium sulfate.

The solvent was removed to afford an oily residue (8.0 g), which was treated with ether. The crystalline product was collected by filtration to give 2,3-dehydro-4-ethoxycarbonylaminothiophane-1,1-dioxide (7.8 g). M.P. 100°–103°C. Recrystallization from a mixture of ether and ethyl acetate afforded pure cyrstals. M.P. 106°–107.5°C.

C. Preparation of
2,3-dehydro-4-aminothiophane-1,1-dioxide hydrobromide

A solution of 2,3-dehydro-4-ethoxycarbonylaminothiophane-1,1-dioxide (5g) in 47% aqueous hydrobromic acid (50 ml) was refluxed for 2.5 hours. The resulting solution was concentrated under reduced pressure, and the residue was treated with methanol (10 ml). The crystalline product was collected by filtration to give 2,3-dehydro-4-aminothiophane-1,1-dioxide hydrobromide (5.0 g). M.P. 258°C. Recrystallization from a mixture of methanol and water gave pure crystals. M.P. 260°–262°C (decomp.).

D. Preparation of
cis-3,4-ureylenethiophane-1,1-dioxide

A mixture of 2,3-dehydro-4-aminothiophane-1,1-dioxide hydrobromide (2.0 g) and potassium isocyanate (1.5 g) in water (12 ml) was refluxed for 3 hours. After cooling, the reaction mixture was allowed to stand overnight below 10°C. The precipitate was collected by filtration and dried to give cis-3,4-ureylenethiophane-1,1-dioxide (767 mg). Recrystallization from water afforded pure crystals. M.P. 318°–320°C (decomp.).

EXAMPLE 2

A. Preparation of
3-chloro-4-aminothiophane-1,1-dioxide hydrobromide

3-Chloro-4-ethoxycarbonylaminothiophane-1,1-dioxide (2 g) was dissolved in 47% aqueous hydrobromic acid (20 ml), and the resultant solution was refluxed for 2 hours and then concentrated under reduced pressure. The precipitate was collected by filtration, recrystallized from methanol and dried to give 3-chloro-4-aminothiophane-1,1-dioxide hydrobromide (1.56 g) as crude crystals. Recrystallization from methanol gave pure crystals. M.P. 188°–189°C.

B. Preparation of
cis-3,4-ureylenethiophane-1,1-dioxide

To a mixture of 3-chloro-4-aminothiophane-1,1-dioxide hydrobromide (1.55 g) and potassium isocyanate (1.5 g) in water (10 ml) was refluxed for 4 hours and then concentrated under reduced pressure to about 5 ml. The precipitated crystals were collected by filtration and recrystallized from water to give cis-3,4-ureylenethiophane-1,1-dioxide (826 mg). M.P. 318°–320°C (decomp.).

EXAMPLE 3

A. Preparation of
2,3-dehydro-4-aminocarbonylaminothiophane-1,1-dioxide

A suspension of 2,3-dehydro-4-aminothiophane-1,1-dioxide hydrobromide (2 g) and potassium isocyanate (0.8 g) in water (12 ml) was refluxed for 2 hours. The reaction mixture was concentrated under reduced pressure, a small amount of water was added thereto, and the resultant mixture was allowed to stand at a temperature below 10°C the precipitated crystals were collected by filtration to give 2,3-dehydro-4-aminocarbonylaminothiophane-1,1-dioxide (932.1 mg) as crude crystals. Recrystallization from water gave pure crystals. M.P. 197°–199°C.

B. Preparation of
cis-3,4-ureylenethiophane-1,1-dioxide 2,3-Dehydro-4-aminocarbonylaminothiophane-1,1-dioxide (176 mg) was added to water (10 ml), and the resultant mixture was refluxed for 1 hour, concentrated under reduced pressure and allowed to stand below 10°C. The precipitated crystals were collected by filtration and recrystallized from water to give cis-3,4-ureylenethiophane-1,1-dioxide (125 mg). M. P. 318°–320°C.

What is claimed is:

1. A process for preparing compounds of the formula

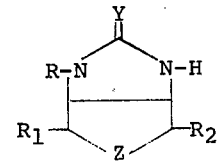

wherein R is a hydrogen atom, a lower alkyl group, a phenyl lower alkyl group or a naphthyl lower alkyl group, $R_1$ and $R_2$ are each a hydrogen atom or an aliphatic hydrocarbon group having not more than 10 carbon atoms or an aliphatic hydrocarbon group having not more than 10 carbon atoms bearing, at the terminal position, a carboxyl group or a lower alkoxycarbonyl group, a phenyl(lower)-alkoxycarbonyl group, a naphthyl(lower)alkoxycarbonyl group, a cyano group, a carboxyl group or a formyl group convertible to a carboxyl group, y is an oxygen atom or a sulfur atom and Z is an oxygen atom, a sulfur atom, a sulfinyl atom or a sulfonyl group, said compounds having a cis-configuration on the ureylene or thioureylene juncture, which process compises reacting a compound of the formula:

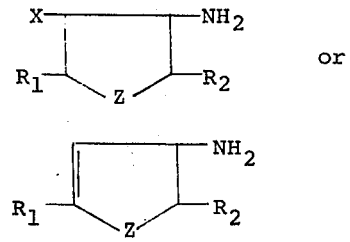

wherein X is a halogen atom, and $R_1$, $R_2$ and Z are each as defined above, with an isocyanate or isothiocyanate of the formula

R—NCY wherein R and Y are each as defined above, or the ammonium, alkali metal or alkaline earth metal salt of isocyanic acid or isothiocyanic acid.

2. The process according to claim 1, wherein the isocyanate or isothiocyanate is an ammonium, alkali metal or alkaline earth metal salt of isocyanic acid or isothiocyanic acid.

3. The process according to claim 1, wherein the isocyanate or isothiocyanate is a lower alkyl, a phenyl(-lower)-alkyl or naphthyl(lower)-alkyl ester of isocyanic or isothiocyanic acid.

4. The process according to claim 1, wherein the isocyanate or isothiocyanate is used in an amount of about 2 to 3 mols to 1 mol of the starting compound.

5. The process according to claim 1, wherein the reaction is carried out at a temperature of from room temperature to the refluxing temperature of the reaction system.

6. The process according to claim 1, wherein the starting compound is the one prepared by treating a compound of the formula:

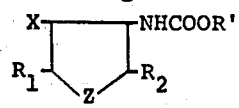 or

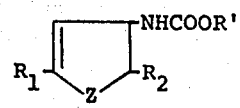

wherein R' is a lower alkyl group, and $R_1$, $R_2$, X and Z are each as defined in claim 1 with a mineral acid.

7. The process according to claim 6, wherein the treatment is carried out in an aqueous medium while refluxing.

* * * * *